United States Patent [19]
Amino et al.

[11] Patent Number: 5,958,496
[45] Date of Patent: Sep. 28, 1999

[54] ASPARTYL DIPEPTIDE AMIDE DERIVATIVES AND SWEETENERS

[75] Inventors: Yusuke Amino; Ryoichiro Nakamura; Tadashi Takemoto, all of Kawasaki, Japan

[73] Assignee: Ajinomoto Co., Inc., Tokyo, Japan

[21] Appl. No.: 08/890,993

[22] Filed: Jul. 10, 1997

[30] Foreign Application Priority Data

Jul. 10, 1996 [JP] Japan ..................................... 8-180485
Mar. 26, 1997 [JP] Japan ..................................... 9-072969

[51] Int. Cl.$^6$ .......................... A23L 1/236; C07C 229/00
[52] U.S. Cl. .......................... 426/548; 562/433; 562/442; 562/450
[58] Field of Search .............................. 426/548; 562/433, 562/442, 450

[56] References Cited

U.S. PATENT DOCUMENTS 5,795,612   8/1998   Takemoto et al. ...................... 426/548

FOREIGN PATENT DOCUMENTS 0 691 346    1/1996   European Pat. Off. .
WO 94 00028  1/1994   WIPO .

*Primary Examiner*—Leslie Wong
*Attorney, Agent, or Firm*—Oblon, Spivak, McClelland, Maier & Neustadt, P.C.

[57] ABSTRACT

Novel aspartyldipeptidoamides and salts thereof. The apartyldipeptides are useful as a low-calorie sweetener for food and beverage products and have excellent taste and chemical stability.

28 Claims, No Drawings

ASPARTYL DIPEPTIDE AMIDE DERIVATIVES AND SWEETENERS

BACKGROUND OF THE INVENTION

1. Field of the Invention

The present invention relates to novel aspartyl dipeptide amide derivatives that are useful as a low-calorie sweetener for food and beverage products.

2. Discussion of the Background

In recent years, eating habits have improved to a great extent, and weight gain caused by excessive consumption of sugar as well as health problems associated with this weight gain have been at issue. Therefore, the development of a low-calorie sweetener to replace sugar has been a major goal. Aspartame is a widely used sweetener which has excellent safety and sweetness properties. However, aspartame contains an ester linkage and, as a result, is unstable. In order to improve the stability and the sweetness intensity, aspartyl-D-amino acid amide derivatives lacking an ester linkage have been investigated, see, for example, U.S. Pat. Nos. 4,411,925 and 5,286,509. French Patent No. 2,697,844 describes aspartyldipeptide derivatives in which an alkyl group has been introduced into an amino group which exhibit an extremely high degree of sweetness. However, these compounds still lack the desired stability properties.

SUMMARY OF THE INVENTION

An object of the present invention is to provide novel aspartyl dipeptide amide derivatives and salts thereof which are chemically stable and intensely sweet.

It is another object of the present invention to provide a low-containing sweetener containing the dipeptide amides of the present invention as an active ingredient.

It is another object to provide a method of sweetening a food and/or beverage product with a chemically stable, low-calorie sweetener.

In order to solve the above-mentioned problems, the present inventors have assiduously conducted investigations with respect to amine components of various aspartyl dipeptide amides having a satisfactory stability, and have consequently found compounds which exhibit a higher degree of sweetness than conventional aspartyl dipeptide amides. This finding has led to the completion of the present invention.

The objects of the present invention are accomplished with an aspartyldipeptide amide of formula (I):

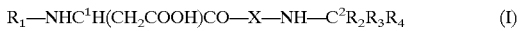

wherein

R$_1$ is a hydrogen atom or a hydrocarbon group having from 1 to 13 carbon atoms;

R$_2$ and R$_3$ are each, independently, an alkyl group having from 1 to 3 carbon atoms, or C$^2$, R$_2$ and R$_3$ together form a cycloalkyl group having from 3 to 6 carbon atoms, or R$_2$ is a hydrogen atom and R$_3$ represents an alkylthioalkyl group having from 2 to 7 carbon atoms, an alkylsulfinylalkyl group having from 2 to 7 carbon atoms, an alkylsulfonylalkyl group having from 2 to 7 carbon atoms or an alkoxycarbonylmethyl group having from 2 to 7 carbon atoms;

R$_4$ is a phenyl group, a benzyl group, a cyclohexyl group, a cyclohexylmethyl group, a phenyl group substituted at the 2-, 3- or 4-position with a substituent selected from the group consisting of F, Cl, Br, I, a hydroxyl group, an alkoxy group having from 1 to 6 carbon atoms, a cyano group, a nitro group, an acetyl group, an amino group and an acetylamino group, a phenyl group substituted at the position 2- and 3-positions or in the 3- and 4-positions with a substituent selected from the group consisting of a methylenedioxy group, a trimethylene group and a tetramethylene group, a 2-, 3- or 4-pyridyl group, a 2- or 3-furyl group, or a 2- or 3-thienyl group;

X is an α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-S-methylcysteine, D-methionine, D-phenylglycine, D-furylglycine and L-furylglycine, or X is a residue of a cyclic or acyclic α,α-dialkylamino acid having from 3 to 6 carbon atoms;

the configuration at the C$^1$-position is (S);

the configuration at the C$^2$-position is (R) or (S) when at least two of R$_2$, R$_3$ and R$_4$ are different, or a salt thereof.

A more complete appreciation of the invention and many of the attendant advantages thereof will be readily obtained as the same becomes better understood by reference to the following detailed description.

DETAILED DESCRIPTION OF THE INVENTION

The novel aspartyl dipeptide amides of the present invention are the derivatives of formula (I) and salts thereof. The present invention is also directed to compositions which contain one or a mixture of two or more of the dipeptide amides of formula (I).

In formula (I), R$_1$ is a hydrogen atom or a hydrocarbon group having from 1 to 13 carbon atoms. The hydrocarbon group may be saturated or unsaturated and it may have any structure, such as linear, branched, cyclic or any form of mixed structure. Preferably, R$_1$ is a hydrogen atom or a branched hydrocarbon group having 3 to 8 carbon atoms. More preferably, R$_1$ is a hydrogen atom or a 3,3-dimethylbutyl group.

R$_2$ and R$_3$ may each be, independently, an alkyl group having from 1 to 3 carbon atoms. When either of these groups have 3 carbon atoms, they may each be, independently of the other, linear, branched or cyclic. When R$_2$ and R$_3$ are each alkyl, they are preferably both methyl groups.

Alternatively, C$^2$, R$_2$ and R$_3$ together may form a cycloalkyl group. Preferably, the cycloalkyl group has 3 to 6 carbon atoms. Preferred cycloalkyl groups include cyclobutyl, cyclopentyl and cyclohexyl groups. In these compounds, the C$^2$-position may be achiral.

In another embodiment, R$^2$ is a hydrogen atom and R$^3$ is an alkylthioalkyl group, an alkylsulfinylalkyl group, an alkylsulfonylalkyl group or an alkoxycarbonylmethyl group. Preferably, these groups have 2 to 7 carbon atoms. Particularly preferred examples of such groups include methylthiomethyl and methoxycarbonylmethyl groups.

Preferred examples of the R$_4$ group include phenyl, cyclohexyl, 4-methoxyphenyl, 4-hydroxyphenyl, 4-methylphenyl and 2,3-methylenedioxyphenyl groups.

X represents an amino acid residue. It is to be understood that the amino group of the amino acid residue represented by X forms an amide bond with the carboxylic acid group bonded to C$^1$ of the adjacent L-Asp residue (i.e., —C$^1$—CO—NH—). The carboxylic acid group of the amino acid residue represented by X forms an amide bond with the amino group bonded to C$^2$ (i.e., —NH—CO—C$^2$—).

The configuration at the $C^1$ carbon is (S). The configuration at $C^2$ may be (R) or (S) when at least two of $R_2$, $R_3$ and $R_4$ are different. When two of $R_2$, $R_3$ and $R_4$ are the same, the $C^2$ carbon atom is not a chiral center.

The present invention also includes mixtures of two or more different dipeptide amides of formula (I). The mixture may contain two or more different dipeptides in which one or more of $R_1$, $R_2$, $R_3$, $R_4$ and X are different in the dipeptides. The present invention also includes stereoisomeric mixtures of dipeptides in which $R_1$, $R_2$, $R_3$ and $R_4$ and X are the same chemical groups, but the dipeptides differ in stereochemistry at the $C^\alpha$ of the amino acid represented by X and/or the $C^2$ carbon. For example, a mixture of two dipeptides where X represents a D-furylglycine residue in the first dipeptide and an L-furylglycine residue in the second dipeptide. Another example is a first dipeptide having the (R) configuration at $C^2$ and a second dipeptide where the configuration at $C^2$ is (S). Mixtures of this type can include any proportion of the individual stereoisomers. Particularly preferred stereoisomeric mixtures include those where the relative amount of each stereoisomer is 95:100 to 1:1.

The present inventions also includes the salts dipeptide (I). Examples of the salts of the compounds in the present invention include salts with alkali metals such as sodium and potassium; salts with alkaline-earth metals such as calcium and magnesium; salts with amines such as monoethanolamine; salts with inorganic acids such as hydrochloric acid and sulfuric acid; and salts with organic acids such as citric acid and acetic acid.

The aspartyl dipeptide amide derivatives of the present invention may be prepared by any of the well-known peptide synthesis methods, see, for example, Basis of Peptide Synthesis and Experiments Thereof, by Izumiya et al., Maruzen, Jan. 20, 1985, incorporated herein by reference. That is, a desired α-L-aspartyl-α-amino acid amide can be formed by first condensing an α-amino acid containing a protected amino group with the corresponding amine, then removing the protective group, condensing the resulting amino acid amide with L-aspartic acid in which the carboxylic acid in the β-position and the amino group are protected to form a dipeptide amide and then removing the protective groups, or by converting L-aspartic acid in which the carboxylic acid in the β-position and the amino group are protected as an active ester, reacting this ester with an α-amino acid, then reacting the reaction mixture with the corresponding amine to obtain a dipeptide amide, and thereafter removing the protective groups.

An N-alkyl-α-L-aspartyl-α-amino acid amide can be formed by reductively alkylating an α-L-aspartyl-α-amino acid amide with an aldehyde and a reducing agent (for example, $NaB(OAc)_3H$) [Tetrahedron Letters, by A. F. Abdel-Magid et al., 31, 5595 (1990), incorporated herein by reference], or reductively alkylating an α-L-aspartyl-α-amino acid amide obtained by protecting a carboxylic acid in the β-position of aspartic acid with an aldehyde and a reducing agent and then removing the protective group. However, the method of forming the compounds of the present invention is not limited thereto.

A β-alkylthioamine used in the compounds of the present invention can be formed by the method described in the literature [Tetrahedron Letters, by B. G. Donner, 36, 1223, (1995) or Tetrahedron Asymmetry, by G. A. Cran et al., 6, 1553 (1995), both incorporated herein by reference]. However, the method is not limited thereto.

β-Phenyl-β-alanine used in the compounds of the present invention may be formed by a known method from benzaldehyde, ammonium acetate and malonic acid and be resolved into optically active substances by the method described in the literature [Chem. Ber., by E. Fischer et al., 43, 2020 (1910) or Tetrahedron, by H. H. Wasserman et al., 39, 2459 (1983), both incorporated herein by reference]. However, the method is not limited thereto.

As a result of the sensory evaluation, it was found that the compounds of the present invention and the salts thereof have a strong sweetness and their sweetness qualities are similar to that of sugar in terms of taste. The compounds of the present invention may be 100 to 6,000 times as sweet as sugar, preferably 200 to 6,000, more preferably 500 to 6,000 and, most preferably, 1,000 to 5,500 times as sweet as sugar. For example, the degree of sweetness of α-L-aspartyl-D-α-aminobutyric acid (R)-α-methylthiomethylbenzylamide was approximately 4,000 times that of sugar, the degree of sweetness of α-L-aspartyl-D-valine (R)-α-methylthiomethylbenzylamide was approximately 3,000 times that of sugar, the degree of sweetness of α-L-aspartyl-D-isoleucine (R)-α-methylthiomethylbenzylamide was approximately 5,000 times that of sugar, the degree of sweetness of N-3,3-dimethylbutyl-α-L-aspartyl-D-valine (R)-α-methylthiomethylbenzylamide was approximately 5,000 times that of sugar, the degree of sweetness of α-L-aspartyl-D-valine (S)-α-methoxycarbonylmethylbenzylamide was approximately 1,500 times that of sugar and the degree of sweetness of α-L-aspartyl-D-valine-α-phenylcyclopentylamide was approximately 1,200 times that of sugar.

The peptides of the present invention may be 2 to 15 times as stable as aspartame when measured in a phosphate buffer of pH 3 at 70° C. This range in stability as compared to aspartame includes all specific values and subranges therebetween. The half-lives (in a phosphate buffer of pH 3 at 70° C.) of α-L-aspartyl-D-valine (R)-α-methylthiomethylbenzylamide, α-L-aspartyl-D-isoleucine (R)-α-methylthiomethylbenzylamide and α-L-aspartyl-D-valine (S)-α-methoxycarbonylmethylbenzylamide in an acidic aqueous solution were approximately 220 hours, 650 hours and 139 hours respectively. The compounds of the present invention are far more stable as compared to aspartame, which had a half-life of approximately 23 hours, under the same test conditions.

The configurations of the aspartyl dipeptide derivatives formed and the results of the sensory evaluation thereof are shown in Table 1.

TABLE 1

Structure of aspartyl[1] dipeptide amide derivatives and degree of sweetness.

| X | $R_1$ | $C^2$ position[2] | $R_2$ | $R_3$ | $R_4$ | degrees of sweetness[3] |
|---|---|---|---|---|---|---|
| D-Ala | H | (R) | H | $CH_2SCH_3$ | Ph | 1000 |
| D-Abu | H | (R) | H | $CH_2SCH_3$ | Ph | 4000 |
| D-Val | H | (R) | H | $CH_2SCH_3$ | Ph | 3000 |
| D-Ile | H | (R) | H | $CH_2SCH_3$ | Ph | 5000 |
| D-Val | 3,3-Dimethylbutyl | (R) | H | $CH_2SCH_3$ | Ph | 5000 |

TABLE 1-continued

Structure of asparty[1] dipeptide amide derivatives and degree of sweetness.

| X | $R_1$ | $C^2$ position[2] | $R_2$ | $R_3$ | $R_4$ | degrees of sweetness[3] |
|---|---|---|---|---|---|---|
| D-Abu | H | (RS) | H | $CH_2CO_2CH_3$ | Ph | 800 |
| D-Val | H | (S) | H | $CH_2CO_2CH_3$ | Ph | 1500 |
| D-Abu | H | (RS) | H | $CH_2CO_2CH_3$ | 4-$CH_3$O—Ph | 200 |
| D-Abu | H | (RS) | H | $CH_2CO_2CH_3$ | 2,3-$CH_2P_2$—Ph | 250 |
| D-Abu | H | (RS) | H | $CH_2CO_2CH_3$ | 4-HO-Ph | 200 |
| D-Abu | H | (RS) | H | $CH_2CO_2CH_3$ | 4-$CH_3$—Ph | 200 |
| D-Abu | H | (RS) | H | $CH_2CO_2CH_3$ | c-$C_6H_{11}$ | 700 |
| D-Val | H | (RS) | H | $CH_2CO_2CH_3$ | c-$C_6H_{11}$ | 400 |
| D-Abu | 3,3-Dimethylbutyl | (RS) | H | $CH_2CO_2CH_3$ | Ph | 1250 |
| D-Val | 3,3-Dimethylbutyl | (RS) | H | $CH_2CO_2CH_3$ | Ph | 1250 |
| D-Abu | 3,3-Dimethylbutyl | (RS) | H | $CH_2CO_2CH_3$ | c-$C_6H_{11}$ | 1250 |
| D-Val | H | — | $CH_3$ | $CH_3$ | Ph | 500 |
| D-Ile | H | — | $CH_3$ | $CH_3$ | Ph | 250 |
| D-Abu | H | — | —$CH_2CH_2CH_2CH_2$— | | Ph | 750 |
| D-Val | H | — | —$CH_2CH_2CH_2CH_2$— | | Ph | 1200 |

[1]The configurations of $C^1$ of the Asp residue are (S).
[2]Configuration at the $C^2$ position.
[3]Degree of sweetness relative to a degree of sweetness of a 4% aqueous sucrose solution.
[4]Abu = α-aminobutyric acid.

The dipeptide amides of formula (I) may be used to sweeten food and/or beverage products. The dipeptide amides of the present invention are preferably used as a substitute for sugar in food and beverage products. The effective amount of the dipeptides needed for a sweetening effect may vary depending on the degree of sweetness of a particular dipeptide as compared to sugar and the desired taste in the sweetened product. Generally, the dipeptide or mixture thereof may comprise 0.01 to 25% by weight of the sweetened food and/or beverage.

When the compounds of the present invention or the salts thereof are used as a sweetener, they may be used in combination with other sweeteners, as long as they are compatible with the additional sweeteners. Suitable additional sweeteners include sugar, sugar alcohols, acesultame k, aspartame and saccharin.

Having generally described this invention, a further understanding can be obtained by reference to certain specific examples which are provided herein for purposes of illustration only and are not intended to be limiting unless otherwise specified.

EXAMPLES

Example 1

α-L-aspartyl-D-valine (R)-α-methylthiomethylbenzylamide

A solution (35 ml) of 4-N HCl/dioxane was added to 2.65 (10.0 mmols) of N-tert-butoxycarbonyl-(R)-α-methylthiomethylbenzylamine, and the mixture was stirred at room temperature for 1 hour. The reaction solution was concentrated under reduced pressure, and the residue was concentrated with the addition of 30 ml of ether to obtain (R)-α-methylthiomethylbenzylamine hydrochloride in a quantitative yield.

N-tert-butoxycarbonyl-D-valine (2.39 g, 11.0 mmols) and 10.0 mmols of the above-obtained (R)-α-methylthiomethylbenzylamine hydrochloride were dissolved in 60 ml of methylene chloride. Triethylamine (1.53 ml, 11.0 mmols), 2.11 g (11.0 mmols) of water-soluble carbodiimide hydrochloride and 1.49 g (11.0 mmols) of HOBt were added to the solution while being cooled to 0° C. The mixture was stirred for 1 hour while being cooled, and then overnight at room temperature. After the reaction mixture was concentrated under reduced pressure, 100 ml of water were added to the residue, and the solution was extracted twice with 100 ml of ethyl acetate. The organic layer was washed twice with a 5% citric acid aqueous solution, with 50 ml of a saturated aqueous solution of sodium chloride, twice with a 5% sodium hydrogencarbonate aqueous solution and with 50 ml of a saturated aqueous solution of sodium chloride. The organic layer was dried over anhydrous magnesium sulfate and then filtered. The filtrate was concentrated under reduced pressure to obtain N-tert-butoxycarbonyl-D-valine (R)-α-methylthiomethylbenzylamide as a solid in a quantitative yield.

A solution (35 ml) of 4-N HCl/dioxane was added to 10.0 mmols of the above-obtained N-tert-butoxycarbonyl-D-valine (R)-α-methylthiomethylbenzylamide, and the mixture was stirred at room temperature for 1 hour. The reaction solution was concentrated under reduced pressure, and the residue was further concentrated with the addition of 30 ml of ether. The residue was dissolved in 60 ml of methylene chloride, and 5.18 g (11.0 mmols) of N-tert-butoxycarbonyl-L-aspartic acid-β-tert-butyl ester dicyclohexylamine salt were then added thereto. Water-soluble carbodiimide hydrochloride (2.11 g, 11.0 mmols) and 1.49 g (11.0 mmols) of HOBt were added thereto while being cooled to 0° C. The mixture was stirred for 1 hour while being cooled and then overnight at room temperature. After the reaction mixture was concentrated under reduced pressure, 100 ml of water were added to the residue, and the solution was extracted twice with 100 ml of ethyl acetate. The organic layer was washed twice with a 5% citric acid aqueous solution, with 50 ml of a saturated aqueous solution of sodium chloride, twice with a 5% sodium hydrogencarbonate aqueous solution, and with 50 ml of a saturated aqueous solution of sodium chloride. The organic layer was dried over anhydrous magnesium sulfate, and then filtered. The filtrate was concentrated under reduced pressure, and purified with PTLC to obtain 5.09 g (9.47 mmols) of N-tert-butoxycarbonyl-β-O-tert-butyl-α-L-aspartyl-D-valine (R)-α-methylthiomethylbenzylamide as a viscous oil.

A solution (45 ml) of 4-N HCl/dioxane was added to 5.09 g (9.47 mmols) of N-tert-butoxycarbonyl-β-O-tert-butyl-α-L-aspartyl-D-valine (R)-α-methylthiomethyl-benzylamide, and the mixture was stirred at room temperature for 2 hours. The reaction solution was concentrated under reduced pressure, and the mixture was stirred with the addition of 50 ml of ether. Subsequently, the supernatant was removed by decantation, and the residue was dried under reduced pressure. The residue was dissolved in 50 ml of water, and insoluble material was removed by filtration. To the filtrate were added 50 ml of methanol and 2 ml of 28% ammonia water, and the solution was concentrated under reduced pressure. The residue was dissolved in a small amount of water and 200 ml of methanol, and 2 g of activated carbon were added thereto. The mixture was stirred at 50° C. for a while. The activated carbon was removed by filtration, and the filtrate was concentrated to approximately one-fourth of its original volume. The crystals precipitated were collected by filtration, washed with a small amount of water, and dried under reduced pressure to give 2.80 g (7.34 mmols) of α-L-aspartyl-D-valine (R)-α-methylthiomethylbenzylamide as a solid.

$^1$HNMR (DMSO-$d_6$) δ: 0.86 (d, 3H), 0.90 (d, 3H), 2.03 (s, 3H), 2.00–2.10 (m, 1H), 2.20 (dd, 1H), 2.42 (dd, 1H), 2.75–2.84 (m, 2H), 3.75 (dd, 1H), 4.27 (brt, 1H), 4.96 (q, 1H), 7.20–7.40 (m, 5H), 8.43 (brd, 1H), 8.59 (d, 1H).

ESI-MS: 382.2 (MH$^+$).

Degree of sweetness (relative to sugar): 3,000 times.

Example 2

α-L-aspartyl-D-alanine (R)-α-methylthiomethylbenzylamide

Example 1 was repeated except that N-tert-butoxycarbonyl-D-alanine was used instead of N-tert-butoxycarbonyl-D-valine to give α-L-aspartyl-D-alanine (R)-α-methylthiomethylbenzylamide as a solid in a total yield of 40.0%.

$^1$HNMR (DMSO-$d_6$) δ: 1.30 (d, 3H), 2.06 (s, 3H), 2.29 (dd, 1H), 2.49 (dd, 1H), 2.74–2.88 (m, 2H), 3.69 (q, 1H), 4.32–4.41 (m, 1H), 4.94–5.02 (m, 1H), 7.25–7.41 (m, 5H), 8.50 (brd, 1H), 8.55 (d, 1H).

ESI-MS: 354.3 (MH$^+$).

Degree of sweetness (relative to sugar): 1,000 times.

Example 3

α-L-aspartyl-D-α-aminobutyric acid (R)-α-methylthiomethylbenzylamide

Example 1 was repeated except that N-tert-butoxycarbonyl-D-α-aminobutyric acid dicyclohexylamine salt was used instead of N-tert-butoxycarbonyl-D-valine to give α-L-aspartyl-D-α-aminobutyric acid (R)-α-methylthiomethylbenzylamide as a solid in a total yield of 53.4%.

$^1$HNMR (DMSO-$d_6$) δ: 0.87 (t, 3H), 1.52–1.68 (m, 1H), 1.68–1.72 (m, 1H), 2.03 (s, 3H), 2.25 (dd, 1H), 2.44 (dd, 1H), 2.72–2.85 (m, 2H), 3.72 (dd, 1H), 4.27 (brq, 1H), 4.95 (q, 1H), 7.20–7.38 (m, 5H), 8.46 (brd, 1H), 8.58 (d, 1H).

ESI-MS: 368.3 (MH$^+$).

Degree of sweetness (relative to sugar): 4,000 times.

Example 4

α-L-aspartyl-D-isoleucine (R)-α-methylthiomethylbenzylamide

Example 1 was repeated except that N-tert-butoxycarbonyl-D-isoleucine was used instead of N-tert-butoxycarbonyl-D-valine to give α-L-aspartyl-D-isoleucine (R)-α-methylthiomethylbenzylamide as a solid in a total yield of 62.8%.

$^1$HNMR (DMSO-$d_6$) δ: 0.84 (t, 3H), 0.90 (d, 3H), 1.04–1.17 (m, 1H), 1.39–1.49 (m, 1H), 1.78–1.87 (m, 1H), 2.04 (s, 3H), 2.20 (dd, 1H), 2.44 (dd, 1H), 2.80 (d, 2H), 3.75 (dd, 1H), 4.30 (brt, 1H), 4.97 (dd, 1H), 7.23–7.40 (m, 5H), 8.48 (brd, 1H), 8.64 (d, 1H).

ESI-MS: 396.3 (MH$^+$).

Degree of sweetness (relative to sugar): 5,000 times.

Example 5

α-L-aspartyl-D-valine (S)-α-methoxycarbonylmethylbenzylamide

N-tert-butoxycarbonyl-D-valine (5.34 g, 24.6 mmols) and 5.31 g (24.6 mmols) of (RS)-α-methoxycarbonylmethylbenzylamine hydrochloride (S:R= 2:1) were suspended in 100 ml of methylene chloride, and the suspension was maintained at 0° C. Triethylamine (3.78 ml, 27.1 mmols), 5.20 g (27.1 mmols) of water-soluble carbodiimide hydrochloride and 3.66 g (27.1 mmols) of HOBt were added thereto, and the mixture was stirred for 1 hour while being cooled and then overnight at room temperature. The reaction mixture was concentrated under reduced pressure, and 150 ml of water were then added to the residue. The solution was extracted twice with 100 ml of ethyl acetate. The organic layer was washed twice with 100 ml of a 5% citric acid aqueous solution, with 100 ml of a saturated aqueous solution of sodium chloride, twice with a 5% sodium hydrogencarbonate aqueous solution and with 100 ml of a saturated aqueous solution of sodium chloride. The organic layer was dried over anhydrous magnesium sulfate, and magnesium sulfate was then removed by filtration. The filtrate was concentrated under reduced pressure to obtain 9.27 g (24.5 mmols) of N-tert-butoxycarbonyl-D-valine (RS)-α-methoxycarbonylmethylbenzylamide as a solid.

A solution (60 ml) of 4-N HCl/dioxane were added to 9.27 g (24.5 mmols) of N-tert-butoxycarbonyl-D-valine (RS)-α-methoxycarbonylmethylbenzylamide, and the mixture was stirred at room temperature for 1 hour. The reaction solution was concentrated under reduced pressure, and the residue was further concentrated with the addition of 50 ml of ether. To the residue were added 100 ml of methylene chloride and 8.75 g (24.5 mmols) of N-benzyloxycarbonyl-L-aspartic acid-β-benzyl ester, and the mixture was maintained at 0° C. Triethylamine (3.75 ml, 26.9 mmols), 5.16 g (26.9 mmols) of water-soluble carbodiimide hydrochloride and 3.64 g (26.9 mmols) of HOBt were added thereto. The resulting solution was stirred for 1 hour while being cooled and then overnight at room temperature. One hundred milliliters of water were added to the reaction mixture, and the solution was extracted twice with 100 ml of ethyl acetate. The organic layer was washed twice with 100 ml of a 5% citric acid aqueous solution, with 100 ml of a saturated aqueous solution of sodium chloride, twice with 100 ml of a 5% sodium hydrogencarbonate aqueous solution and with 100 ml of a saturated aqueous solution of sodium chloride. The organic layer was dried over anhydrous magnesium sulfate, and magnesium sulfate was then removed by filtration. The filtrate was concentrated under reduced pressure to obtain 13.6 g (22.0 mmols) of N-benzyloxycarbonyl-β-O-benzyl-L-aspartyl-D-valine (RS)-α-methoxycarbonylmethyl-benzylamide as a solid.

N-benzyloxycarbonyl-β-O-benzyl-L-aspartyl-D-valine (RS)-α-methoxycarbonyl-methylbenzylamide (13.6 g, 22.0 mmols) was suspended in a mixed solvent of 150 ml of methanol and 5 ml of water, and 3.0 g of 5% palladium on carbon having a water content of 50% were added thereto. The mixture was reduced at 50° C. for 5 hours under a hydrogen atmosphere. The catalyst was removed by filtration, and the filtrate was concentrated under reduced pressure. The resulting residue was recrystallized from a mixture of methanol and water, and dried to give 3.18 g (8.08 mmols) of α-L-aspartyl-D-valine (S)-α-methoxycarbonylmethylbenzylamide.

$^1$HNMR(DMSO-$d_6$) δ: 0.81 (d, 3H), 0.83 (d, 3H), 1.90–2.00 (m, 1H), 2.19 (dd, 1H), 2.40 (dd, 1H), 2.70–2.83 (m, 2H), 3.55 (s, 3H), 3.69–3.75 (m, 1H), 4.18 (brs, 1H), 7.20–7.35 (m, 5H), 8.39 (brs, 1H), 8.64 (d, 1H).

ESI-MS: 394.3 ($MH^+$).

Degree of sweetness (relative to sugar): 1,500 times.

Example 6

α-L-aspartyl-D-valine (RS)-α-cyclohexyl-β-methoxycarbonylethylamide

Example 5 was repeated except that (RS)-α-cyclohexyl-β-methoxycarbonyl-ethylamine hydrochloride was used instead of (RS)-α-methoxycarbonylmethyl-benzylamine hydrochloride to give α-L-aspartyl-D-valine (RS)-α-cyclohexyl-β-methoxycarbonylethylamide as a solid in a total yield of 54.6%.

$^1$HNMR (DMSO-$d_6$) δ: 0.79 (d, 3H), 0.82 (d, 3H), 0.80–1.75 (m, 13H), 1.85–2.03 (m, 1H), 2.20–2.58 (m, 4H), 3.54 (s, 3H), 3.73–3.80 (m, 1H), 3.97 (brs, 1H), 4.18 (brs, 1H), 7.85 (d, 0.5H), 7.89 (d, 0.5H), 8.32 (brs, 1H).

ESI-MS: 400.3 ($MH^+$).

Degree of sweetness (relative to sugar): 400 times.

Example 7

α-L-aspartyl-D-α-aminobutyric acid α-phenylcyclopentylamide

Example 5 was repeated except that N-tert-butoxycarbonyl-D-α-aminobutyric acid dicyclohexylamine salt was used instead of N-tert-butoxycarbonyl-D-valine and α-phenylcyclopentylamine instead of (RS)-α-methoxycarbonylmethylbenzylamine hydrochloride, respectively, to give α-L-aspartyl-D-α-aminobutyric acid phenylcyclopentylamide as a solid in a total yield of 54.9%.

$^1$HNMR (DMSO-$d_6$) δ: 0.79 (t, 3H), 1.45–1.57 (m, 2H), 1.55–1.93 (m, 6H), 2.18–2.50 (m, 4H), 3.69 (m, 1H), 4.25 (brd, 1H), 7.10–7.35 (m, 5H), 8.12 (s, 1H), 8.30 (brd, 1H).

ESI-MS: 362.3 ($MH^+$).

Degree of sweetness (relative to sugar): 750 times.

Example 8

α-L-aspartyl-D-valine α-phenylcyclopentylamide

Example 5 was repeated except that α-phenylcyclopentylamine was used instead of (RS)-α-methoxycarbonylmethylbenzylamine hydrochloride to give α-L-aspartyl-D-valine α-phenylcyclopentylamide as a solid in a total yield of 61.9%.

$^1$HNMR (DMSO-$d_6$) δ: 0.76 (d, 3H), 0.80 (d, 3H), 1.65–2.00 (m, 7H), 2.15–2.50 (m, 4H), 3.73 (m, 1H), 4.23 (brs, 1H), 7.10–7.35 (m, 5H), 8.14 (s, 1H), 8.25 (brd, 1H).

ESI-MS: 376.3 ($MH^+$).

Degree of sweetness (relative to sugar): 1,200 times.

Example 9

α-L-aspartyl-D-isoleucine α,α-dimethylbenzylamide

Example 5 was repeated except that N-tert-butoxycarbonyl-D-isoleucine was used instead of N-tert-butoxycarbonyl-D-valine and α,α-dimethylbenzylamine instead of (RS)-α-methoxycarbonylmethylbenzylamine hydrochloride respectively to give α-L-aspartyl-D-isoleucine α,α-dimethylbenzylamide as a solid in a total yield of 55.8%.

$^1$HNMR (DMSO-$d_6$) δ: 0.82 (t, 3H), 0.83 (d, 3H), 0.96–1.11 (m, 1H), 1.29–1.41 (m, 1H), 1.53 (s, 3H), 1.56 (s, 3H), 1.69–1.80 (m, 1H), 2.29 (dd, 1H), 2.48 (dd, 1H), 3.79 (dd, 1H), 4.28 (brt, 1H), 7.13–7.33 (m, 5H), 8.24 (s, 1H), 8.32 (brd, 1H).

ESI-MS: 364.3 ($MH^+$).

Degree of sweetness (relative to sugar): 250 times.

Example 10

α-L-aspartyl-D-α-aminobutyric acid (RS)-α-methoxycarbonylmethylbenzylamide (RS)-α-methoxycarbonylmethylbenzylamine hydrochloride (216 mg, 1.0 mmol) and 443 mg (1.0 mmol) of N-benzyloxycarbonyl-β-O-benzyl-L-aspartyl-D-α-aminobutyric acid were dissolved in 20 ml of methylene chloride. Water-soluble carbodiimide hydrochloride (211 mg, 1.1 mmols), 149 mg (1.1 mmols) of HOBt and 0.153 ml (1.1 mmols) of triethylamine were added thereto while being cooled to 0° C. The mixture was stirred for 1 hour while being cooled and then overnight at room temperature. After the reaction mixture was concentrated under reduced pressure, 50 ml of water were added to the residue, and the solution was extracted twice with 30 ml of ethyl acetate. The organic layer was washed twice with 25 ml of a 5% citric acid aqueous solution, with 25 ml of a saturated aqueous solution of sodium chloride, twice with 25 ml of a 5% sodium hydrogencarbonate aqueous solution and with 25 ml of a saturated aqueous solution of sodium chloride. The organic layer was dried over anhydrous magnesium sulfate, and then filtered. The filtrate was concentrated under reduced pressure to obtain 603 mg (0.997 mmols) of N-benzyloxycarbonyl-β-O-benzyl-L-aspartyl-D-α-aminobutyric acid (RS)-α-methoxycarbonylmethylbenzylamide as a solid.

N-benzyloxycarbonyl-β-O-benzyl-L-aspartyl-D-α-aminobutyric acid (RS)-methoxycarbonylmethylbenzylamide (603 mg, 0.997 mmols) was suspended in 30 ml of methanol and 2 ml of water, and 200 mg of 5% palladium on carbon having a water content of 50% were added thereto. The solution was reduced under a hydrogen atmosphere at room temperature for 2 hours. The catalyst was removed by filtration, and the filtrate was concentrated under, reduced pressure. The solid material precipitated was collected by filtration, and dried to give 289 mg (0.76 mmols) of α-L-aspartyl-D-α-aminobutyric acid (RS)-α-methoxycarbonylmethylbenzylamide.

$^1$HNMR (DMSO-$d_6$) δ: 0.73 (t, 1.5H), 0.82 (t, 1.5H), 1.40–1.70 (m, 2H), 2.15–2.30 (m, 1H), 2.39–2.50 (m, 1H), 2.70–2.85 (m, 2H), 3.54 (s, 3H), 4.19 (brs, 1H), 5.15–5.28 (m, 1H), 7.20–7.40 (m, 5H), 8.35 (brs, 1H), 8.58 (brd, 1H).

ESI-MS: 380.3 ($MH^+$).

Degree of sweetness (relative to sugar): 800 times.

Example 11

α-L-aspartyl-D-α-aminobutyric acid (RS)-α-methoxycarbonylmethyl-4-methoxybenzylamide Example 10 was repeated except that (RS)-α-methoxycarbonylmethyl-4-methoxybenzylamine hydrochloride was used instead of (RS)-α-methoxycarbonylmethylbenzylamine hydrochloride to give α-L-aspartyl-D-α-aminobutyric acid (RS)-α-methoxycarbonylmethyl-4-methoxybenzylamide as a solid in a total yield of 44.0%.

$^1$HNMR (DMSO-$d_6$) δ: 0.72 (t, 1.5H), 0.81 (t, 1.5H), 1.40–1.65 (m, 2H), 2.22–2.34 (m, 1H), 2.45–2.53 (m, 1H), 2.68–2.82 (m, 2H), 3.54 (s, 3H), 3.72 (s, 3H), 3.69–3.77 (m, 1H), 4.16–4.20 (m, 1H), 5.10–5.20 (m, 1H), 6.86 (d, 1H), 6.87 (d, 1H), 7.21 (d, 1H), 7.24 (d, 1H), 8.39 (brd, 1H), 8.51 (d, 1H).

ESI-MS: 410.3 (MH$^+$).

Degree of sweetness (relative to sugar): 200 times.

Example 12

α-L-aspartyl-D-α-aminobutyric acid (RS)-α-methoxycarbonylmethyl-2,3-methylenedioxybenzylamide Example 10 was repeated except that (RS)-α-methoxycarbonylmethyl-2,3-methylenedioxybenzylamine hydrochloride was used instead of (RS)-α-methoxycarbonylmethylbenzylamine hydrochloride to give α-L-aspartyl-D-α-aminobutyric acid (RS)-α-methoxycarbonylmethyl-2,3-methylenedioxybenzylamide as a solid in a total yield of 53.4%.

$^1$HNMR (DMSO-$d_6$) δ: 0.73 (t, 1.5H), 0.81 (t, 1.5H), 1.40–1.70 (m, 2H), 2.15–2.30 (m, 1H), 2.40–2.55 (m, 1H), 2.66–2.82 (m, 2H), 3.55 (s, 3H), 3.67 (brs, 1H), 4.18 (brs, 1H), 5.05–5.18 (m, 1H), 5.98 (s, 2H), 6.73–6.92 (m, 3H), 8.34 (brs, 1H), 8.47 (brd, 1H).

ESI-MS: 424.3 (MH$^+$).

Degree of sweetness (relative to sugar): 250 times.

Example 13

α-L-aspartyl-D-α-aminobutyric acid (RS)-α-methoxycarbonylmethyl-4-hydroxybenzylamide Example 10 was repeated except that (RS)-α-methoxycarbonylmethyl-4-benzyloxybenzylamine hydrochloride was used instead of (RS)-α-methoxycarbonylmethylbenzylamine hydrochloride to give a-L-aspartyl-D-α-aminobutyric acid (RS)-α-methoxycarbonylmethyl-4-hydroxybenzyl amide as a solid in a total yield of 37.4%.

$^1$HNMR (DMSO-$d_6$) δ: 0.72 (t, 1.5H), 0.81 (t, 1.5H), 1.40–1.70 (m, 2H), 2.24–2.38 (m, 1H), 2.45–2.56 (m, 1H), 2.65–2.82 (m, 2H), 3.53 (s, 3H), 3.70–3.80 (m, 1H), 4.19 (brs, 1H), 5.03–5.15 (m, 1H), 6.67 (d, 1H), 6.69 (d, 1H), 7.09 (d, 1H), 7.12 (d, 1H), 8.37 (brs, 1H), 8.45 (d, 0.5H), 8.48 (d, 0.5H).

ESI-MS: 396.3 (MH$^+$).

Degree of sweetness (relative to sugar): 200 times.

Example 14

L-aspartyl-D-α-aminobutyric acid (RS)-α-methoxycarbonylmethyl-4-methylbenzylamide Example 10 was repeated except that (RS)-α-methoxycarbonylmethyl-4-methylbenzylamine hydrochloride was used instead of (RS)-α-methoxycarbonylmethylbenzylamine hydrochloride to give α-L-aspartyl-D-α-aminobutyric acid (RS)-α-methoxycarbonylmethyl-4-methylbenzylamide as a solid in a total yield of 61.4%.

$^1$HNMR (DMSO-$d_6$) δ: 0.73 (t, 1.5H), 0.82 (t, 1.5H), 1.40–1.70 (m, 2H), 2.16–2.30 (m, 1H), 2.26 (s, 3H), 2.40–2.50 (m, 1H), 2.65–2.84 (m, 2H), 3.54 (s, 3H), 3.66–3.74 (m, 1H), 4.20 (brd, 1H), 5.10–5.23 (m, 1H), 7.08–7.24 (m, 4H), 8.37 (brs, 1H), 8.53 (brd, 1H).

ESI-MS: 394.3 (MH$^+$).

Degree of sweetness (relative to sugar): 200 times

Example 15

α-L-aspartyl-D-α-aminobutyric acid (RS)-α-cyclohexyl-β-methoxycarbonylethylamide Example 10 was repeated except that (RS)-α-cyclohexyl-β-methoxycarbonylethylamine hydrochloride was used instead of (RS)-α-methoxycarbonylmethylbenzylamine hydrochloride to give α-L-aspartyl-D-α-aminobutyric acid (RS)-α-cyclohexyl-β-methoxycarbonylethylamide as a solid in a total yield of 87.2%.

$^1$HNMR (DMSO-$d_6$) δ: 0.80 (t, 3H), 0.82–1.75 (m, 13H), 2.23–2.35 (m, 2H), 2.45–2.60 (m, 2H), 3.53 (s, 3H), 3.71–3.77 (m, 1H), 3.95 (brs, 1H), 4.19 (brs, 1H), 7.82 (d, 1H), 8.35 (brd, 1H).

ESI-MS: 386.3 (MH$^+$).

Degree of sweetness (relative to sugar): 700 times.

Example 16

Synthesis of α-L-aspartyl-D-valine α,α-dimethylbenzylamide

Example 10 was repeated except that N-benzyloxycarbonyl-β-O-benzyl-L-aspartyl-D-valine was used instead of N-benzyloxycarbonyl-β-O-benzyl-L-aspartyl-D-α-aminobutyric acid and α,α-dimethylbenzylamine instead of (RS)-α-methoxycarbonylmethylbenzylamine hydrochloride respectively to give α-L-aspartyl-D-valine α,α-dimethylbenzylamide as a solid in a total yield of 27.6%.

$^1$HNMR (DMSO-$d_6$) δ: 0.80 (d, 3H), 0.85 (d, 3H), 1.54 (s, 3H), 1.57 (s, 3H), 1.94–2.07 (m, 1H), 2.22 (dd, 1H), 2.44 (dd, 1H), 3.74 (dd, 1H), 4.25 (brs, 1H), 2.44 (dd, 1H), 3.74 (dd, 1H), 4.25 (brs, 1H), 7.13–7.34 (m, 5H), 8.23 (s, 1H), 8.33 (brd, 1H).

ESI-MS: 350.3 (MH$^+$).

Degree of sweetness (relative to sugar): 500 times.

Example 17

N-3,3-dimethylbutyl-α-L-aspartyl-D-valine (R)-α-methylthiomethylbenzylamide

α-L-aspartyl-D-valine (R)-α-methylthiomethyl- benzylamide (381 mg, 1.0 mmol) was suspended in 20 ml of THF, and 0.13 ml (1.0 mmol) of 3,3-dimethylbutyl aldehyde and 0.06 ml (1.0 mmol) of acetic acid were added thereto. The solution was maintained at 0° C., and 318 mg (1.5 mmols) of NaB(OAc)$_3$H were added thereto. The mixture was stirred at 0° C. for 1 hour and further overnight at room temperature. The reaction solution was concentrated under reduced pressure, and the residue was neutralized with a 5% sodium hydrogencarbonate aqueous solution. The reaction solution was concentrated, and then purified with silica-gel column chromatography (eluted with a mixture of ethyl acetate, chloroform and methanol at a ratio of 3:1:1.5) to give 180 mg (0.39 mmols) of N-3,3-dimethylbutyl-α-L-aspartyl-D-valine (R)-α-methylthiomethyl-benzylamide as a solid.

$^1$HNMR (DMSO-d$_6$) δ: 0.79 (s, 9H), 0.80–0.89 (m, 6H), 1.26–1.36 (m, 2H), 2.01 (s, 3H), 2.01–2.08 (m, 1H), 2.21 (dd, 1H), 2.35 (dd, 1H), 2.41–2.44 (m, 2H), 2.72–2.80 (m, 2H), 3.40 (dd, 1H), 4.23 (brt, 1H), 4.96 (q, 1H), 7.20–7.35 (m, 5H), 8.26 (d, 1H), 8.62 (d, 1H).

ESI-MS: 466.4 (MH$^+$).

Degree of sweetness (relative to sugar): 5,000 times.

Example 18

N-3,3-dimethylbutyl-α-L-aspartyl-D-α-aminobutyric acid (RS)-α-methoxycarbonylmethylbenzylamide N-tert-butoxycarbonyl-D-α-aminobutyric acid dicyclohexylamine salt (769 mg, 2.0 mmols) and 431 mg (2.0 mmols) of (RS)-α-methoxycarbonylmethylbenzylamine hydrochloride were dissolved in 25 ml of methylene chloride. Water-soluble carbodiimide hydrochloride (383 mg, 2.2 mmols) and 297 mg (2.2 mmols) of HOBt were added thereto while being cooled to 0° C. The mixture was stirred for 1 hour while being cooled and then overnight at room temperature. After the reaction mixture was concentrated under reduced pressure, 50 ml of water were added to the residue, and the solution was extracted twice with 50 ml of ethyl acetate. The extract was washed twice with 25 ml of a 5% citric acid aqueous solution, 25 ml of a saturated aqueous solution of sodium chloride, twice with 25 ml of a 5% sodium hydrogencarbonate aqueous solution and with 25 ml of a saturated aqueous solution of sodium chloride. The organic layer was dried over anhydrous magnesium sulfate, and then filtered. The filtrate was concentrated under reduced pressure to obtain 730 mg (2.0 mmols) of N-tert-butoxycarbonyl-D-α-aminobutyric acid (RS)-α-methoxycarbonylmethylbenzylamide as a solid.

A solution (10 ml) of 4-N HCl/dioxane were added to 730 mg (2.0 mmols) of N-tert-butoxycarbonyl-D-α-aminobutyric acid (RS)-α-methoxycarbonylmethylbenzylamide, and the mixture was stirred at room temperature for 1 hour. The reaction solution was concentrated under reduced pressure. The residue was further concentrated with the addition of 30 ml of ether. The resulting residue was dissolved in 25 ml of methylene chloride and 0.31 ml (2.2 mmols) of triethylamine, and 647 mg (2.0 rmnol s) of N-tert-butoxycarbonyl-L-aspartic acid-β-benzyl ester were then added thereto. Water-soluble carbodiimide hydrochloride (383 mg, 2.2 mmols) and 297 mg (2.2 mmol) of HOBt were added thereto while being cooled. The mixture was stirred for 1 hour while being cooled and then overnight at room temperature. After the reaction mixture was concentrated under reduced pressure, 50 ml of water were added to the residue. The solution was extracted twice with 50 ml of ethyl acetate. The extract was washed twice with 25 ml of a 5% citric acid aqueous solution, with 25 ml of a saturated aqueous solution of sodium chloride, twice with 25 ml of a 5% sodium hydrogencarbonate aqueous solution and with 25 ml of a saturated aqueous solution of sodium chloride. The organic layer was dried over anhydrous magnesium sulfate, and then filtered. The filtrate was concentrated under reduced pressure to obtain 742 mg (2.0 mmols) of N-tert-butoxycarbonyl-β-O-benzyl-L-aspartyl-D-α-aminobutyric acid (RS)-α-methoxycarbonylmethylbenzylamide as a solid.

A solution (10 ml) of 4-N HCl/dioxane were added to 742 mg (2.0 mmols) of N-tert-butoxycarbonyl-β-O-benzyl-L-aspartyl-D-α-aminobutyric acid (RS)-α-methoxycarbonylmethylbenzylamide, and the mixture was stirred at room temperature for 1 hour. The reaction solution was concentrated under reduced pressure, and 30 ml of a 5% sodium hydrogencarbonate aqueous solution were added to the residue. The mixture was extracted twice with 50 ml of ethyl acetate. The organic layer was washed with a saturated aqueous solution of sodium chloride, dried over anhydrous magnesium sulfate, and filtered. The filtrate was concentrated under reduced pressure to give 893 mg (1.90 mmols) of β-O-benzyl-L-aspartyl-D-α-aminobutyric acid (RS)-α-methoxycarbonylmethylbenzylamide as a viscous oil.

β-O-benzyl-L-aspartyl-D-α-aminobutyric acid (RS)-α-methoxycarbonyl-methylbenzylamide (893 mg, 1.90 mmols) was dissolved in 15 ml of THF, and the solution was maintained at 0° C. To this solution were added 0.11 ml (1.90 mmols) of acetic acid, 0.24 ml (1.90 mmols) of 3,3-dimethylbutyl aldehyde and 605 mg (2.85 mmols) of NaB(OAc)$_3$H. The mixture was stirred at 0° C. for 1 hour and further overnight at room temperature. To the reaction solution were added 30 ml of a saturated aqueous solution of sodium hydrogencarbonate, and the mixture was extracted twice with 50 ml of ethyl acetate. The organic layer was washed with a saturated aqueous solution of sodium chloride, dried over anhydrous magnesium sulfate, and then filtered. The filtrate was concentrated under reduced pressure. The residue was purified with PTLC to obtain 820 mg (1.48 mmols) of N-3,3-dimethylbutyl-β-O-benzyl-L-aspartyl-D-α-aminobutyric acid (RS)-α-methoxycarbonylmethylbenzylamide as a solid.

N-3,3-dimethylbutyl-β-O-benzyl-L-aspartyl-D-α-aminobutyric acid (RS)-α-methoxycarbonylmethylbenzylamide (820 mg, 1.48 mmols) was dissolved in a mixed solvent of 35 ml of methanol and 2 ml of water, and 400 mg of 5% palladium on carbon having a water content of 50% were added thereto. The mixture was reduced under a hydrogen atmosphere for 2 hours. Ten milliliters of water were added thereto, and the catalyst was removed by filtration. The filtrate was concentrated under reduced pressure. The residue was dried under reduced pressure to give 604 mg (1.30 mmols) of N-3,3 -dimethylbutyl-α-L-aspartyl-D-α-aminobutyric acid (RS)-α-methoxycarbonyl-methylbenzylamide as a solid.

$^1$HNMR (DMSO-d$_6$) δ: 0.70–0.85 (m, 3H), 0.79 (s, 4.5 H), 0.87 (s, 4.5H), 1.30–1.70 (m, 4H), 2.55–2.85 (m, 6H), 3.54 (s, 1.5H), 3.56 (s, 1.5H), 3.81 (brs, 1H), 4.18–4.23 (m, 1H), 5.13–5.30 (m, 1H), 7.20–7.35 (m, 5H), 8.48 (d, 0.5H), 8.52 (d, 0.5H), 8.63 (d, 1H).

ESI-MS: 464.4 (MH$^+$).

Degree of sweetness (relative to sugar): 1,250 times.

Example 19

N-3,3-dimethylbutyl-α-L-aspartyl-D-valine (RS)-α-methoxycarbonylmethylbenzylamide Example 18 was repeated except that N-tert-butoxycarbonyl-D-valine was used instead of N-tert-butoxycarbonyl-D-α-aminobutyric acid dicyclohexylamine salt to give N-3,3-dimethylbutyl-α-L-aspartyl-D-valine (RS)-α-methoxycarbonylmethylbenzylamide as a solid in a total yield of 75.7%.

$^1$HNMR (DMSO-d$_6$) δ: 0.70–0.80 (m, 6H), 0.76 (s, 4.5H), 0.87 (s, 4.5H), 1.28–1.53 (m, 2H), 1.90–2.00 (m, 1H), 2.50–2.85 (m, 6H), 3.53 (s, 1.5H), 3.55 (s, 1.5H), 3.85–3.92

(m, 1H), 4.15–4.22 (m, 1H), 5.15–5.30 (m, 1H), 7.20–7.35 (m, 5H), 8.43 (d, 0.5H), 8.46 (d, 0.5H), 8.66 (brd, 1H).

ESI-MS: 478.5 (MH⁺).

Degree of sweetness (relative to sugar): 1,250 times.

Example 20

N-3,3-dimethylbutyl-α-L-aspartyl-D-α-aminobutyric acid (RS)-α-cyclohexyl-β-methoxycarbonylethylamide Example 18 was repeated except that (RS)-α-cyclohexyl-β-methoxycarbonyl-ethylamine hydrochloride was used instead of (RS)-α-methoxycarbonylmethyl-benzylamine hydrochloride to give N-3,3-dimethylbutyl-α-L-aspartyl-D-α-aminobutyric acid (RS)-α-cyclohexyl-β-methoxycarbonylethylamide as a solid in a total yield of 65.7%.

¹HNMR (DMSO-d₆) δ: 0.75–0.85 (m, 3H), 0.87 (s, 9H), 0.90–1.75 (m, 13H), 2.25–2.42 (m, 1H), 2.50–2.80 (m, 5H), 3.54 (s, 3H), 3.80–4.00 (m, 2H), 4.10–4.23 (m, 1H), 7.89 (d, 1H), 8.47 (d, 0.5H), 8.54 (d, 0.5H).

ESI-MS: 470.4 (MH⁺).

Degree of sweetness (relative to sugar): 1,250 times.

Obviously, numerous modifications and variations of the present invention are possible in light of the above teachings. It is therefore to be understood that within the scope of the appended claims, the invention may be practiced otherwise than as specifically described herein.

This application is based on Japanese Patent Application No. 180485/1996, filed Jul. 10, 1996, and 072969/1997, filed Mar. 26, 1997, and both incorporated herein by reference in their entirety.

What is claimed as new and is desired to be secured by Letters Patent of the United States is:

1. An aspartyl dipeptide of formula (I):

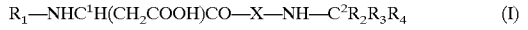

$$R_1\text{—NHC}^1\text{H(CH}_2\text{COOH)CO—X—NH—C}^2R_2R_3R_4 \quad (I)$$

wherein $R_1$ is a hydrogen atom or a hydrocarbon group having from 1 to 13 carbon atoms;

$R_2$ and $R_3$ are each, independently, an alkyl group having from 1 to 3 carbon atoms, or $C^2$, $R_2$ and $R_3$ together form a cycloalkyl group having from 3 to 6 carbon atoms, or $R_2$ is a hydrogen atom and $R_3$ is an alkylthioalkyl group having from 2 to 7 carbon atoms, an alkylsulfinylalkyl group having from 2 to 7 carbon atoms, an alkylsulfonylalkyl group having from 2 to 7 carbon atoms or an alkoxycarbonylmethyl group having from 2 to 7 carbon atoms;

$R_4$ is a phenyl group, a benzyl group, a cyclohexyl group, a cyclohexylmethyl group, a phenyl group substituted at the 2-, 3- or 4-position with a substituent selected from the group consisting of F, Cl, Br, I, a hydroxyl group, an alkoxy group having from 1 to 6 carbon atoms, a cyano group, a nitro group, an acetyl group, an amino group and an acetylamino group, a phenyl group substituted at the position 2- and 3-positions or in the 3- and 4-positions with a substituent selected from the group consisting of a methylenedioxy group, a trimethylene group and a tetramethylene group, a 2-, 3- or 4-pyridyl group, a 2- or 3-furyl group, or a 2- or 3-thienyl group;

X is an α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-S-methylcysteine, D-methionine, D-phenylglycine, D-furylglycine and L-furylglycine, or X is a residue of a cyclic or acyclic α, α-dialkylamino acid having from 3 to 6 carbon atoms;

the configuration at the $C^1$-position is (S);

the configuration at the $C^2$-position is (R) or (S) when at least two of $R_2$, $R_3$ and $R_4$ are different, or a salt thereof.

2. The dipeptide of claim 1, wherein $C^2$, $R_2$ and $R_3$ together form a cycloalkyl group having from 3 to 6 carbon atoms.

3. The dipeptide of claim 1, wherein $R_2$ is a hydrogen atom and $R_3$ represents an alkylthioalkyl group having from 2 to 7 carbon atoms, an alkylsulfinylalkyl group having from 2 to 7 carbon atoms, an alkylsulfonylalkyl group having from 2 to 7 carbon atoms or an alkoxycarbonylmethyl group having from 2 to 7 carbon atoms.

4. The dipeptide of claim 1, wherein $R_1$ is a hydrogen atom, X is a D-alanine residue, $R_2$ is a hydrogen atom, $R_3$ is a methylthiomethyl group, and $R_4$ is a phenyl group.

5. The dipeptide of claim 1, wherein $R_1$ is a hydrogen atom, X is a D-α-aminobutyric acid residue, $R_2$ is a hydrogen atom, $R_3$ is a methylthiomethyl group, and $R_4$ is a phenyl group.

6. The dipeptide of claim 1, wherein $R_1$ is a hydrogen atom, X is a D-valine residue, $R_2$ is a hydrogen atom, $R_3$ is a methylthiomethyl group, and $R_4$ is a phenyl group.

7. The dipeptide of claim 1, wherein $R_1$ is a hydrogen atom, X is a D-isoleucine residue, $R_2$ is a hydrogen atom, $R_3$ is a methylthiomethyl group, and $R_4$ is a phenyl group.

8. The dipeptide of claim 1, wherein $R_1$ is a 3,3-dimethylbutyl group, X is a D-valine residue, $R_2$ is a hydrogen atom, $R_3$ is a methylthiomethyl group, and $R_4$ is a phenyl group.

9. The dipeptide of claim 1, wherein $R_1$ is a hydrogen atom, X is a D-α-aminobutyric acid residue, $R_2$ is a hydrogen atom, $R_3$ is a methoxycarbonylmethyl group, and $R_4$ is a phenyl group.

10. The dipeptide of claim 1, wherein $R_1$ is a hydrogen atom, X is a D-valine residue, $R_2$ is a hydrogen atom, $R_3$ is a methoxycarbonylmethyl group, and $R_4$ is a phenyl group.

11. The dipeptide of claim 1, wherein $R_1$ is a hydrogen atom, X is a D-α-aminobutyric acid residue, $R_2$ is a hydrogen atom, $R_3$ is a methoxycarbonylmethyl group, and $R_4$ is a cyclohexyl group.

12. The dipeptide of claim 1, wherein $R_1$ is a hydrogen atom, X is a D-valine residue, $R_2$ is a hydrogen atom, $R_3$ is a methoxycarbonylmethyl group, and $R_4$ is a cyclohexyl group.

13. The dipeptide of claim 1, wherein $R_1$ is a 3,3-dimethylbutyl group, X is a D-α-aminobutyric acid residue, $R_2$ is a hydrogen atom, $R_3$ is a methoxycarbonylmethyl group, and $R_4$ is a phenyl group.

14. The dipeptide of claim 1, wherein $R_1$ is a 3,3-dimethylbutyl group, X is a D-valine residue, $R_2$ is a hydrogen atom, $R_3$ is a methoxycarbonylmethyl group, and $R_4$ is a phenyl group.

15. The dipeptide of claim 1, wherein $R_1$ is a 3,3-dimethylbutyl group, X is a D-α-aminobutyric acid residue, $R_2$ is a hydrogen atom, $R_3$ is a methoxycarbonylmethyl group, and $R_4$ is a cyclohexyl group.

16. The dipeptide of claim 1, wherein $R_1$ is a hydrogen atom, X is a D-valine residue, $R_2$ and $R_3$ are each methyl groups, and $R_4$ and is a phenyl group.

17. The dipeptide of claim 1, wherein $R_1$ is a hydrogen atom, X is a D-α-aminobutyric acid residue, $C^2$, $R_2$ and $R_3$ together form a cyclopentyl group, and $R_4$ is a phenyl group.

18. The dipeptide of claim 1, wherein $R_1$ is a hydrogen atom, X is a D-valine residue, $C^2$, $R_2$ and $R_3$ together form a cyclopentyl group, and $R_4$ is a phenyl group.

19. A sweetener composition, comprising:

a first dipeptide of formula (I) as defined in claim 1; and a second dipeptide of formula (I) as defined in claim 1.

20. The composition of claim 19, wherein at least two of $R_2$, $R_3$ and $R_4$ are different in the first and second dipeptide;

$R_1$, $R_2$, $R_3$ and $R_4$ in the first dipeptide are each, respectively, the same as $R_1$, $R_2$, $R_3$ and $R_4$, respectively, in the second dipeptide;

the configuration at $C^2$ in the first peptide is different from the configuration at $C^2$ in the second peptide; and X in the first dipeptide is the same as or different from X in the second dipeptide.

21. A method of sweetening a food and/or a beverage comprising adding to a food and/or a beverage an effective amount of an aspartyl dipeptide of formula (I):

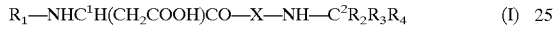

$$R_1-NHC^1H(CH_2COOH)CO-X-NH-C^2R_2R_3R_4 \quad (I)$$

wherein $R_1$ is a hydrogen atom or a hydrocarbon group having from 1 to 13 carbon atoms;

$R_2$ and $R_3$ are each, independently, an alkyl group having from 1 to 3 carbon atoms, or $C^2$, $R_2$ and $R_3$ together form a cycloalkyl group having from 3 to 6 carbon atoms, or $R_2$ is a hydrogen atom and $R_3$ represents an alkylthioalkyl group having from 2 to 7 carbon atoms, an alkylsulfinylalkyl group having from 2 to 7 carbon atoms, an alkylsulfonylalkyl group having from 2 to 7 carbon atoms or an alkoxycarbonylmethyl group having from 2 to 7 carbon atoms;

$R_4$ is a phenyl group, a benzyl group, a cyclohexyl group, a cyclohexylmethyl group, a phenyl group substituted at the 2-, 3- or 4-position with a substituent selected from the group consisting of F, Cl, Br, I, a hydroxyl group, an alkoxy group having from 1 to 6 carbon atoms, a cyano group, a nitro group, an acetyl group, an amino group and an acetylamino group, a phenyl group substituted at the position 2- and 3-positions or in the 3- and 4-positions with a substituent selected from the group consisting of a methylenedioxy group, a trimethylene group and a tetramethylene group, a 2-, 3- or 4-pyridyl group, a 2- or 3-furyl group, or a 2- or 3-thienyl group;

X is an α-amino acid residue selected from the group consisting of D-alanine, D-α-aminobutyric acid, D-norvaline, D-valine, D-norleucine, D-leucine, D-isoleucine, D-alloisoleucine, D-t-leucine, D-serine, D-O-methylserine, D-threonine, D-O-methylthreonine, D-allothreonine, D-O-methylallothreonine, D-S-methylcysteine, D-methionine, D-phenylglycine, D-furylglycine and L-furylglycine, or X is a residue of a cyclic or acyclic α, α-dialkylamino acid having from 3 to 6 carbon atoms;

the configuration at the $C^1$-position is (S);

the configuration at the $C^2$-position is (R) or (S) when at least two of $R_2$, $R_3$ and $R_4$ are different, or a salt thereof.

22. The dipeptide of claim 1, which is said salt thereof.

23. The dipeptide of claim 22, which is a salt of an alkali metal or alkaline earth metal.

24. The dipeptide of claim 22, wherein the alkali metal is sodium or potassium and the alkaline-earth metal is calcium or magnesium.

25. The dipeptide of claim 22, which is a salt of an inorganic acid or an organic acid.

26. The dipeptide of claim 22, wherein the inorganic acid is hydrochloric acid or sulfuric acid and the organic acid is citric acid or acetic acid.

27. The dipeptide of claim 22, which is a salt of amine.

28. A sweetened food, comprising a food and an amount of the dipeptide of claim 1 effective to sweeten the food.

* * * * *